US012362071B2

(12) United States Patent
Krummen et al.

(10) Patent No.: US 12,362,071 B2
(45) Date of Patent: Jul. 15, 2025

(54) COMPUTATIONAL CARDIAC DEPOLARIZATION AND REPOLARIZATION SIMULATION LIBRARY MAPPING FOR NON-INVASIVE ARRHYTHMIA RISK STRATIFICATION

(71) Applicants: Vektor Medical, Inc., Carlsbad, CA (US); The Regents of the University of California, Oakland, CA (US)

(72) Inventors: David Krummen, San Diego, CA (US); Kurt Hoffmayer, San Diego, CA (US); Christopher Villongco, San Diego, CA (US)

(73) Assignees: The Regents of the University of California; Vektor Medical, Inc.

( * ) Notice: Subject to any disclaimer, the term of this patent is extended or adjusted under 35 U.S.C. 154(b) by 72 days.

(21) Appl. No.: 17/784,975

(22) PCT Filed: Oct. 22, 2021

(86) PCT No.: PCT/US2021/056311
§ 371 (c)(1),
(2) Date: Jun. 13, 2022

(87) PCT Pub. No.: WO2022/087457
PCT Pub. Date: Apr. 28, 2022

(65) Prior Publication Data
US 2023/0005625 A1    Jan. 5, 2023

Related U.S. Application Data

(60) Provisional application No. 63/104,930, filed on Oct. 23, 2020.

(51) Int. Cl.
*G16H 50/50*   (2018.01)
*G16H 20/40*   (2018.01)
(Continued)

(52) U.S. Cl.
CPC ............. *G16H 50/50* (2018.01); *G16H 20/40* (2018.01); *G16H 50/30* (2018.01); *G16H 70/20* (2018.01)

(58) Field of Classification Search
CPC ........ G16H 50/50; G16H 20/40; G16H 50/30; G16H 70/20; G16H 30/40; G16H 40/67; G16H 40/63
See application file for complete search history.

(56) References Cited

U.S. PATENT DOCUMENTS 8,128,569 B1 *   3/2012   Mason ................ A61B 5/0205
                                                                    600/484
9,277,970 B2     3/2016   Mansi et al.
(Continued)

FOREIGN PATENT DOCUMENTS

WO   WO-2017172825 A2   10/2017

OTHER PUBLICATIONS

C. Laurita, Kenneth Robert. "Dynamics of Cardiac Repolarization as a Determinant of Arrhythmia Vulnerability." Order No. 9723515 Case Western Reserve University, 1996 (Year: 1996).*
(Continued)

*Primary Examiner* — Amber A Misiaszek
(74) *Attorney, Agent, or Firm* — Perkins Coie LLP

(57) ABSTRACT

A non-invasive method for cardiac arrhythmia risk stratification may include identifying, based at least on an electrical recording of a patient, a cardiac depolarization simulation and a cardiac repolarization simulation corresponding to an electrical recording of a patient. One or more regions of increased spatial repolarization gradient in which a first area of a myocardium of the patient exhibits a first repolarization rate that differs from a second repolarization rate of a second area of the myocardium by an amount then divided by the spatial distance between the two regions, by a threshold (Continued)

value may be determined based on the cardiac depolarization simulation and the cardiac repolarization simulation. A risk of cardiac arrhythmia for the patient may be determined based a magnitude of the increased spatial repolarization gradient. Moreover, a treatment plan for the patient may be determined based on the magnitude and/or location of the increased spatial repolarization gradient.

49 Claims, 14 Drawing Sheets

(51) Int. Cl.
  *G16H 50/30* (2018.01)
  *G16H 70/20* (2018.01)

(56) References Cited

U.S. PATENT DOCUMENTS

| | | | |
|---|---|---|---|
| 9,474,460 B2 * | 10/2016 | Shakibi Gilani | A61B 5/352 |
| 10,141,077 B2 | 11/2018 | Seegerer et al. | |
| 2005/0234357 A1 * | 10/2005 | Xue | A61B 5/35 |
| | | | 600/510 |
| 2008/0109041 A1 * | 5/2008 | de Voir | A61N 1/37 |
| | | | 607/7 |
| 2010/0217144 A1 | 8/2010 | Brian | |
| 2011/0282227 A1 | 11/2011 | Zhang | |
| 2014/0107507 A1 * | 4/2014 | Ghosh | A61B 5/349 |
| | | | 607/18 |
| 2014/0257122 A1 | 9/2014 | Ong et al. | |
| 2015/0265174 A1 * | 9/2015 | Shakibi Gilani | A61B 5/346 |
| | | | 600/521 |
| 2018/0224427 A1 | 8/2018 | Abi Georges et al. | |

OTHER PUBLICATIONS

Restivo, M., et al. "Spatial Dispersion of Repolarization is a Key Factor in the Arrhythmogenicity of Long QT Syndrome," Journal of Cardiovascular Electrophysiology vol. 15, No. 3, Mar. 2004, 9 pages.

International Search Report and Written Opinion received for Application No. PCT/US21/56311, mailed on Jan. 21, 2022, 16 pages.

* cited by examiner

Control

| | 1 | 2 | 3 | 4 |
|---|---|---|---|---|
| AA | 2.5 | 2 | 0 | 1 |
| AB | 1 | 3 | 2 | 2 |
| AC | 1 | 2.5 | 4.5 | 5 |

| | 1 | 2 | 3 | 4 |
|---|---|---|---|---|
| PA | 0 | 1 | 2 | 2 |
| PB | 0 | 0 | 0 | 2 |
| PC | 1.25 | 1 | 0 | 0 |

Experimental

| Anterior | 1 | 2 | 3 | 4 |
|---|---|---|---|---|
| AA | 3.07 | 34.44 | 15.75 | 8.26 |
| AB | 16.97 | 208.02 | 321.42 | 203.69 |
| AC | 103.43 | 156.93 | 349.2 | 244.8 |

| Post | 1 | 2 | 3 | 4 |
|---|---|---|---|---|
| PA | 2.55 | 3.58 | 26.1 | 29.1 |
| PB | 27.56 | 23.46 | 54.26 | 23.36 |
| PC | 30.77 | 153.87 | 57.23 | 58.93 |

FIG. 14

COMPUTATIONAL CARDIAC DEPOLARIZATION AND REPOLARIZATION SIMULATION LIBRARY MAPPING FOR NON-INVASIVE ARRHYTHMIA RISK STRATIFICATION

RELATED APPLICATION

This application claims priority to U.S. Provisional Application No. 63/104,930, entitled "COMPUTATIONAL CARDIAC DEPOLARIZATION AND REPOLARIZATION SIMULATION LIBRARY MAPPING FOR NON-INVASIVE ARRHYTHMIA RISK STRATIFICATION" and filed on Oct. 23, 2020, the disclosure of which is incorporated herein by reference in its entirety.

TECHNICAL FIELD

The subject matter described herein relates generally to computational modeling and simulations, and more specifically to simulation library mapping for non-invasive arrhythmia mapping and risk stratification.

BACKGROUND

Cardiac arrhythmias are common medical disorders in which abnormal electrical signals in the heart cause the heart to contract in a suboptimal manner. The resulting abnormal heartbeat, or arrhythmia, can occur in the atria of the heart (e.g., atrial fibrillation (AF)) and/or the ventricles of the heart (e.g., ventricular tachycardia (VT) or ventricular fibrillation (VF)). Treatments for cardiac arrhythmias attempt to address the mechanisms driving sustained and/or clinically significant episodes including, for example, stable electrical rotors, recurring electrical focal sources, reentrant electrical circuits, and/or the like. Left untreated, cardiac arrhythmias may cause serious health complications such as morbidity (e.g., syncope, stroke, and/or the like) and mortality (e.g. sudden cardiac death (SCD)).

SUMMARY

Systems, methods, and articles of manufacture, including computer program products, are provided for computational cardiac depolarization and repolarization simulation library mapping for non-invasive arrhythmia risk stratification. In one aspect, there is provided a system for non-invasive arrhythmia risk stratification. The system may include at least one processor and at least one memory storing instructions that cause operations when executed by the at least one processor. The operations may include: identifying, within a computational library, a cardiac depolarization simulation and a cardiac repolarization simulation corresponding to an electrical recording of a patient; determining, based at least on the cardiac depolarization simulation and the cardiac repolarization simulation, one or more regions of increased spatial repolarization gradient in which a first area of a myocardium of the patient exhibits a first repolarization rate that differs from a second repolarization rate of a second area of the myocardium by an amount then divided by the spatial distance between the two regions, by a threshold value; and determining, based at least on a magnitude of the increased spatial repolarization gradient, a risk of cardiac arrhythmia or sudden cardiac death (SCD) for the patient.

In some variations, one or more features disclosed herein including the following features can optionally be included in any feasible combination. The operations may further include determining, based at least on the magnitude of the increased spatial repolarization gradient, a treatment plan for the patient.

In some variations, the treatment plan may be determined to include, based at least the magnitude of the increased spatial repolarization gradient, a cardioverter-defibrillator implantation or an invasive electrophysiology study and ablation.

In some variations, the treatment plan may include determining, based at least on a location of the one or more regions of increased spatial repolarization gradient, a location for a targeted therapy such as radiofrequency catheter ablation, cryoablation, high-frequency ultrasound ablation, laser therapy, or pulsed field ablation.

In some variations, the targeted therapy may include catheter ablation and/or stereotactic ablative radiotherapy (SAbR).

In some variations, the cardiac depolarization simulation may include a ventricular activation simulation, and wherein the cardiac repolarization simulation comprises a ventricular recovery simulation.

In some variations, the operations may further include: generating the computational library to include a plurality of cardiac depolarization simulation and a plurality of cardiac repolarization simulations, the plurality of cardiac depolarization simulation and the plurality of cardiac repolarization simulation corresponding to a variety of cardiac geometries, cardiac orientations, scar configurations, degrees of cardiac fibrosis and scar, depolarization patterns, and/or activation types; and identifying, within the computational library, the cardiac depolarization simulation and the cardiac repolarization simulations corresponding to the electrical recording of the patient.

In some variations, the computational library may be supplemented by clinical patient samples with known arrhythmia substrate source locations to provide additional data for comparison to the electrical recording of the patient.

In some variations, the computational library may include clinical patient samples with known arrhythmia substrate source locations to form reference data for comparison to the electrical recording of the patient.

In some variations, the operations may further include: identifying, based at least on clinical data associated with the patient, a subset of simulations from the computational library that correspond to an anatomy of the patient; and identifying, within the subset of simulations corresponding to the anatomy of the patient, the cardiac depolarization simulation and the cardiac repolarization simulation corresponding to the electrical recording of the patient.

In some variations, the clinical data may include patient demographics.

In some variations, the clinical data may include cardiac imaging data indicating one or more locations of scar tissue, borderzone tissue, and normal tissue, cardiac chamber size, the presence of hypertrophy or dilation, locations of fibrosis, regions of normal and abnormal contractility, and/or regions of wall thinning.

In some variations, the operations may further include: in response to failing to identify the subset of simulations corresponding to the anatomy of the patient, generating, based at least on the clinical data of the patient, a custom computational library that includes one or more cardiac depolarization simulations and/or cardiac repolarization simulations specific to the anatomy of the patient.

In some variations, the operations may further include applying a machine learning model trained to determine that the cardiac depolarization simulation and the cardiac repolarization simulation match the electrical recording of the patient.

In some variations, the machine learning model may include a neural network, a regression model, an instance-based model, a regularization model, a decision tree, a random forest, a Bayesian model, a clustering model, an associative model, a dimensionality reduction model, and/or an ensemble model.

In some variations, the operations may further include applying, to the electrical recording of the patient, one or more of signal processing techniques.

In some variations, the one or more signal processing techniques may include recording, filtering, digitization, transformation, and/or spatial analysis.

In some variations, the electrical recording may include one or more of an electrogram, a vectorgram, an electrocardiogram, an electroencephalogram, or a vectorcardiogram.

In some variations, the electrical recording may further include one or more body surface potential recordings.

In some variations, the electrical recording may include electrocardiogram imaging (ECGi) data including one or more body surface potential recordings.

In some variations, the operations may further include: determining, based at least on the cardiac depolarization simulation and the cardiac repolarization simulation, one or more regions of early activation, slow conduction, independent activation pathways, late activation, protected isthmuses of conduction, and/or conduction block; and determining, based at least on a presence and/or an absence of the one or more regions of early activation, slow conduction, independent activation pathways, late activation, and/or conduction block, the risk of cardiac arrhythmia for the patient.

In some variations, the operations may further include: determining, based at least on the one or more regions of early activation, slow conduction, independent activation pathways, late activation, and/or conduction block, a treatment plan for the patient.

In some variations, the treatment plan may target, individually or in groups, the one or more regions of early activation, slow conduction, independent activation pathways, late activation, and/or conduction block.

In some variations, the treatment plan may be determined to include one or more drug therapies based at least on the presence and/or the absence of the one or more regions of early activation, slow conduction, independent activation pathways, late activation, protected isthmuses of conduction, and/or conduction block.

In another aspect, there is provided a method for non-invasive arrhythmia risk stratification. The method may include: identifying, within a computational library, a cardiac depolarization simulation and a cardiac repolarization simulation corresponding to an electrical recording of a patient; determining, based at least on the cardiac depolarization simulation and the cardiac repolarization simulation, one or more regions of increased spatial repolarization gradient in which a first area of a myocardium of the patient exhibits a first repolarization rate that differs from a second repolarization rate of a second area of the myocardium by an amount then divided by the spatial distance between the two regions, by a threshold value; and determining, based at least on a magnitude of the increased spatial repolarization gradient, a risk of cardiac arrhythmia for the patient.

In some variations, one or more features disclosed herein including the following features can optionally be included in any feasible combination. The operations may further include determining, based at least on the magnitude of the increased spatial repolarization gradient, a treatment plan for the patient.

In some variations, the treatment plan may be determined to include, based at least the magnitude of the increased spatial repolarization gradient, a cardioverter-defibrillator implantation or an invasive electrophysiology study and ablation.

In some variations, the treatment plan may include determining, based at least on a location of the one or more regions of increased spatial repolarization gradient, a location for a targeted therapy.

In some variations, the targeted therapy may include catheter ablation and/or stereotactic ablative radiotherapy (SAbR).

In some variations, the cardiac depolarization simulation may include a ventricular activation simulation, and wherein the cardiac repolarization simulation comprises a ventricular recovery simulation.

In some variations, the method may further include: generating the computational library to include a plurality of cardiac depolarization simulation and a plurality of cardiac repolarization simulation, the plurality of cardiac depolarization simulation and the plurality of cardiac repolarization simulation corresponding to a variety of cardiac geometries, cardiac orientations, scar configurations, degrees of cardiac fibrosis and scar, depolarization patterns, and/or activation types; and identifying, within the computational library, the cardiac repolarization simulation and the cardiac depolarization simulation corresponding to the electrical recording of the patient.

In some variations, the method may further include: identifying, based at least on clinical data associated with the patient, a subset of simulations from the computational library that correspond to an anatomy of the patient; and identifying, within the subset of simulations corresponding to the anatomy of the patient, the cardiac repolarization simulation and the cardiac depolarization simulation corresponding to the electrical recording of the patient.

In some variations, the clinical data may include patient demographics.

In some variations, the clinical data may include cardiac imaging data indicating one or more locations of scar tissue, borderzone tissue, and normal tissue, cardiac chamber size, the presence of hypertrophy or dilation, locations of fibrosis, regions of normal and abnormal contractility, and/or regions of wall thinning.

In some variations, the method may further include: in response to failing to identify the subset of simulations corresponding to the anatomy of the patient, generating, based at least on the clinical data of the patient, a custom computational library that includes one or more cardiac depolarization simulations and/or cardiac repolarization simulations specific to the anatomy of the patient.

In some variations, the method may further include applying a machine learning model trained to determine that the cardiac depolarization simulation and the cardiac repolarization simulation match the electrical recording of the patient.

In some variations, the machine learning model may include a neural network, a regression model, an instance-based model, a regularization model, a decision tree, a random forest, a Bayesian model, a clustering model, an associative model, a dimensionality reduction model, and/or an ensemble model.

In some variations, the method may further include applying, to the electrical recording of the patient, one or more of signal processing techniques.

In some variations, the one or more signal processing techniques may include recording, filtering, digitization, transformation, and/or spatial analysis.

In some variations, the electrical recording may include one or more of an electrogram, a vectorgram, an electrocardiogram, an electroencephalogram, or a vectorcardiogram.

In some variations, the electrical recording may further include one or more body surface potential recordings.

In some variations, the electrical recording may include an electrocardiogram imaging (ECGi) including one or more body surface potential recordings.

In some variations, the method may further include: determining, based at least on the cardiac depolarization simulation and the cardiac repolarization simulation, one or more regions of early activation, slow conduction, independent activation pathways, late activation, protected conduction isthmuses, and/or conduction block; and determining, based at least on a presence and/or an absence of the one or more regions of early activation, slow conduction, independent activation pathways, late activation, protected conduction isthmuses, and/or conduction block, the risk of cardiac arrhythmia for the patient.

In some variations, the method may further include: determining, based at least on the one or more regions of early activation, slow conduction, independent activation pathways, late activation, protected conduction isthmuses, and/or conduction block, a treatment plan for the patient.

In some variations, the treatment plan may target, individually or in groups, the one or more regions of early activation, slow conduction, independent activation pathways, late activation, protected conduction isthmuses, and/or conduction block.

In some variations, the treatment plan may be determined to include one or more drug therapies based at least on the presence and/or the absence of the one or more regions of early activation, slow conduction, independent activation pathways, late activation, protected conduction isthmuses, and/or conduction block.

In another aspect, there is provided a non-transitory computer readable medium storing instructions that cause operations when executed by at least one data processor. The operations may include: identifying, within a computational library, a cardiac depolarization simulation and a cardiac repolarization simulation corresponding to an electrical recording of a patient; determining, based at least on the cardiac depolarization simulation and the cardiac repolarization simulation, one or more regions of increased spatial repolarization gradient in which a first area of a myocardium of the patient exhibits a first repolarization rate that differs from a second repolarization rate of a second area of the myocardium by an amount then divided by the spatial distance between the two regions, by a threshold value; and determining, based at least on a magnitude of the increased spatial repolarization gradient, a risk of cardiac arrhythmia for the patient.

In another aspect, there is provided an apparatus for non-invasive arrhythmia risk stratification. The apparatus may include: means for identifying, within a computational library, a cardiac depolarization simulation and a cardiac repolarization simulation corresponding to an electrical recording of a patient; means for determining, based at least on the cardiac depolarization simulation and the cardiac repolarization simulation, one or more regions of increased spatial repolarization gradient in which a first area of a myocardium of the patient exhibits a first repolarization rate that differs from, and exists in close spatial proximity to, a second repolarization rate of a second area of the myocardium by a threshold value; and means for determining, based at least on a magnitude of the increased spatial repolarization gradient, a risk of cardiac arrhythmia for the patient.

Implementations of the current subject matter can include systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connection including, for example, a connection over a network (e.g. the Internet, a wireless wide area network, a local area network, a wide area network, a wired network, or the like), a direct connection between one or more of the multiple computing systems, and/or the like.

The details of one or more variations of the subject matter described herein are set forth in the accompanying drawings and the description below. Other features and advantages of the subject matter described herein may be apparent from the description and drawings, and from the claims. While certain features of the currently disclosed subject matter are described for illustrative purposes in relation to computational cardiac depolarization and repolarization simulation library mapping for non-invasive arrhythmia risk stratification, it should be readily understood that such features are not intended to be limiting. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 14 depicts an example of a plot comparing the cardiac repolarization spatial heterogeneity of a patient with ventricular arrhythmias against that of a control patient, in accordance with some example embodiments.

When practical, similar reference numbers denote similar structures, features, or elements.

DETAILED DESCRIPTION

Figure 1:
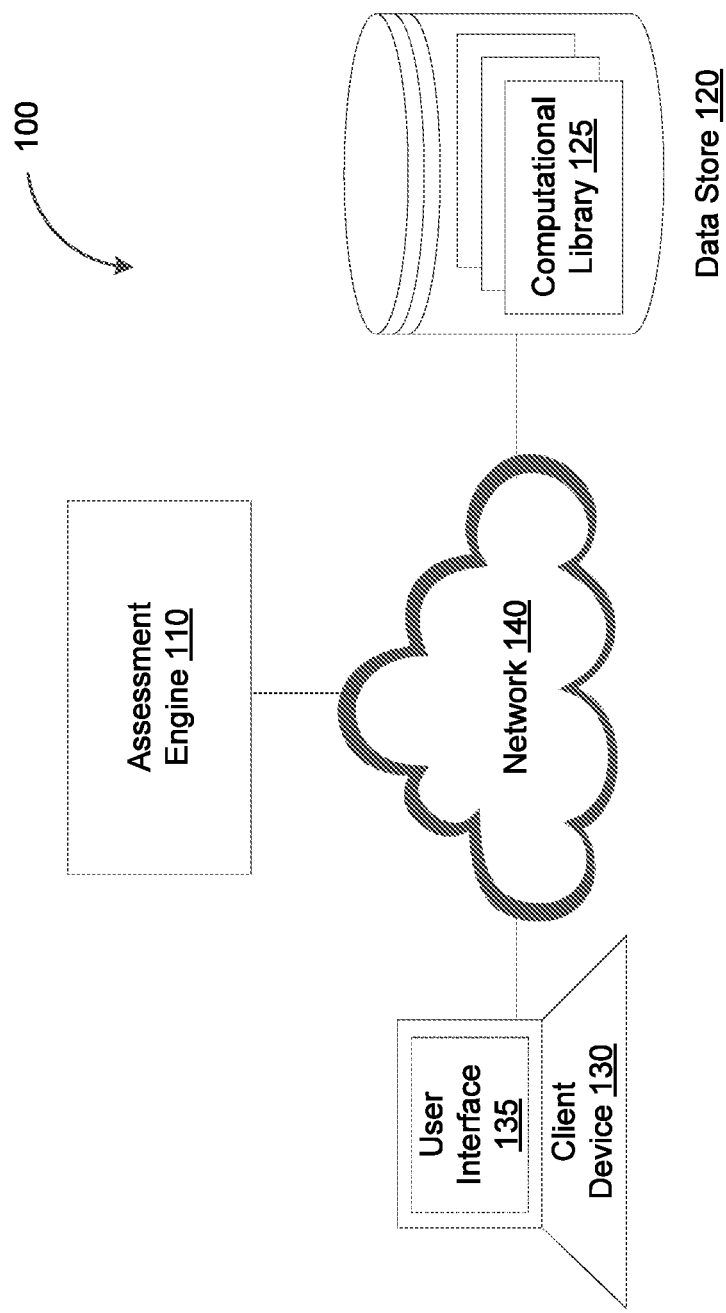
FIG. 1 depicts a system diagram illustrating an example of a risk stratification system, in accordance with some example embodiments.

Sudden cardiac death (SCD) affects approximately 400,000 patients in the United States and 3,000,000 patients worldwide every year. Currently, left ventricular ejection fraction, a technique measuring the volumetric fraction of blood ejected from the left ventricle, is used to assess a patient's risk for ventricular arrhythmias and sudden cardiac death. In many instances, left ventricular ejection fraction may also be used to determine whether the patient is a suitable candidate for an implantable cardioverter-defibrillator implantation or for invasive electrophysiology study and catheter ablation. However, left ventricular ejection fraction has suboptimal sensitivity and specificity for ventricular arrhythmias and sudden cardiac death. Moreover, left ventricular ejection fraction is also be unable to predict mortality from worsening heart failure.

Cardiac arrhythmias (e.g., atrial fibrillation, ventricular tachycardia, ventricular fibrillation) may be treated by targeting the mechanisms driving sustained and/or clinically significant episodes including, for example, stable electrical rotors, recurring electrical focal sources, reentrant electrical circuits, and/or the like. Ablation is one example treatment for cardiac arrhythmias in which radiofrequency, cryogenic temperatures, ultrasound, laser energy, pulsed field ablation, and/or radiation (e.g. stereotactic ablative radiotherapy (SAbR)) may be applied to the source of the cardiac arrhythmia. The resulting lesions may alleviate cardiac arrhythmia by disrupting and/or eliminating the erratic electric signals causing the abnormal heart activation.

A major challenge in arrhythmia management is the difficulty in predicting individual risk for ventricular tachycardia (VT) and ventricular fibrillation (VF). Presently, the majority of ventricular arrhythmia events occur in "low risk" populations. Thus, a large majority of patients (e.g., 55% of men and 65% of women) have sudden cardiac death (SCD) as their first presentation of increased arrhythmia risk. Furthermore, risk stratification in patients with inherited cardiomyopathies remains challenging. The risk of sudden cardiac death in patients with inherited familial cardiomyopathies is contingent on many factors including the electrophysiological alterations (e.g., conduction slowing, action potential morphology and restitution, intracellular calcium handling, and mechanoelectrical feedback) specific to the cardiomyopathy that can serve as a trigger to the arrhythmia and provide the myocardial structural remodeling (e.g., hypertrophy, fibrosis, fibrofatty deposits) that perpetuates the arrhythmia. The variable penetrance and/or unknown significance of many cardiomyopathy variants further complicates the assessment of arrhythmia risk. Traditionally, risk for sudden cardiac death in patients with genetic cardiomyopathies is assessed via left ventricular ejection fraction or scoring criteria. In practice, however, the suboptimal sensitivity and specificity of these conventional methods leave patients uncertain about their arrhythmia risk and suitable treatments (e.g., implantable cardioverter-defibrillator (ICD) therapy or catheter ablation).

Additionally, monitoring the initiation and maintenance of QT-prolonging drug therapies, including antiarrhythmic medications such as dofetilide and sotalol, remains challenging given a patient's individualized responses to sodium or potassium channel blocking agents. Such drug therapies, which delay ventricular recovery (or repolarization), may protract the patient's QT interval. Thus, prior attempts have focused on prolongation of the QT interval or corrected QT (QTc) interval on the patient's surface electrocardiogram. Nevertheless, although these metrics assess important physiologic changes, sensitivity and specificity to accurately monitor QT-prolonging drug therapies remain suboptimal.

In light of the suboptimal sensitivity and specificity of conventional methodologies for assessing the risk of ventricular arrhythmia and methods to identify arrhythmia locations which either initiate or sustained cardiac arrhythmias, various implementations of the present disclosure include a rapid and noninvasive tool that provides a more accurate assessment of ventricular arrhythmia risks across diverse groups of patients and localize regions which may be pro-arrhythmic. In some example embodiments, an assessment engine may be configured to provide a patient-specific assessment of pro-arrhythmic factors. In particular, the assessment engine may stratify the risk of cardiac arrhythmias based on a spatial repolarization gradient, which corresponds to the magnitude by which the refractory period of neighboring regions in the myocardium changes as a function of distance through cardiac tissue. For example, the assessment engine may identify, based at least on adjacent myocardium areas exhibiting above-threshold differences in rates of cardiac repolarization (e.g., a first area of long repolarization that is immediately adjacent to a second area of short repolarization), a potentially pro-arrhythmic condition that is likely to result in an electrical wavebreak, reentry, and life-threatening arrhythmia.

FIG. 1 depicts a system diagram illustrating an example of a risk stratification system 100, in accordance with some example embodiments. Referring to FIG. 1, the risk stratification system 100 may include an assessment engine 110, a data store 120 storing one or more computational libraries 125, and a client device 130. As shown in FIG. 1, the assessment engine 110, the data store 120, and the client device 130 may be communicatively coupled via a network 140. The data store 120 may be a database including, for example, a graph database, an in-memory database, a relational database, a non-SQL (NoSQL) database, and/or the like. The client device 130 may be a processor-based device including, for example, a cellular phone, a smartphone, a tablet computer, a laptop computer, a desktop, a workstation, and/or the like. The network 140 may be a wired network and/or a wireless network including, for example, a wide area network (WAN), a local area network (LAN), a virtual local area network (VLAN), a public land mobile network (PLMN), the Internet, and/or the like.

In some example embodiments, the assessment engine 110 may be configured to determine, based at least on one or more regions of increased spatial repolarization gradient associated with a patient, the patient's risk for cardiac arrhythmias. As used herein, the term "spatial repolarization gradient" may refer to the magnitude by which the refractory period of neighboring regions in the myocardium changes as a function of distance through cardiac tissue. For example, the assessment engine 110 may determine, based at least on the presence of neighboring myocardium areas with above-threshold different rates of cardiac repolarization (e.g., a first area of long repolarization that is immediately adjacent to a second area of short repolarization), the patient as exhibiting a potentially pro-arrhythmic condition that is likely to result in an electrical wavebreak, reentry, and life-threatening arrhythmia.

In some example embodiments, the computational engine 110 may identify, based at least on one or more computational simulations of cardiac depolarization (e.g. ventricular activation) and/or cardiac repolarization (e.g., ventricular recovery), one or more regions of increased spatial repolarization gradient of the patient. The one or more computational simulations may be selected from the computational library 125 stored, for example, at the data store 120. For example, the computational library 125 may include cardiac depolarization simulations (e.g., ventricular activation simulations) for various cardiac geometries, cardiac orientations, scar configurations, degrees of cardiac fibrosis and scar, depolarization patterns, activation types (e.g. left bundle branch block, right bundle branch block, left anterior fascicular block, left posterior fascicular block, premature ventricular complexes, ventricular tachycardia, and ventricular fibrillation), and combinations thereof. Alternatively and/or additionally, the computational library 125 may include cardiac repolarization simulations (e.g., ventricular recovery simulations) for various cardiac geometries, cardiac orientations, scar configurations, degrees of cardiac fibrosis and scar, depolarization patterns, activation types (e.g. left bundle branch block, right bundle branch block, left anterior fascicular block, left posterior fascicular block, premature ventricular complexes, ventricular tachycardia, and ventricular fibrillation), and combinations thereof. In some instances, the computational library 125 may include a first computational library of cardiac depolarization simulations (e.g., ventricular activation simulations) and a second computational library of cardiac repolarization simulations (e.g., ventricular recovery simulations).

Figure 3:
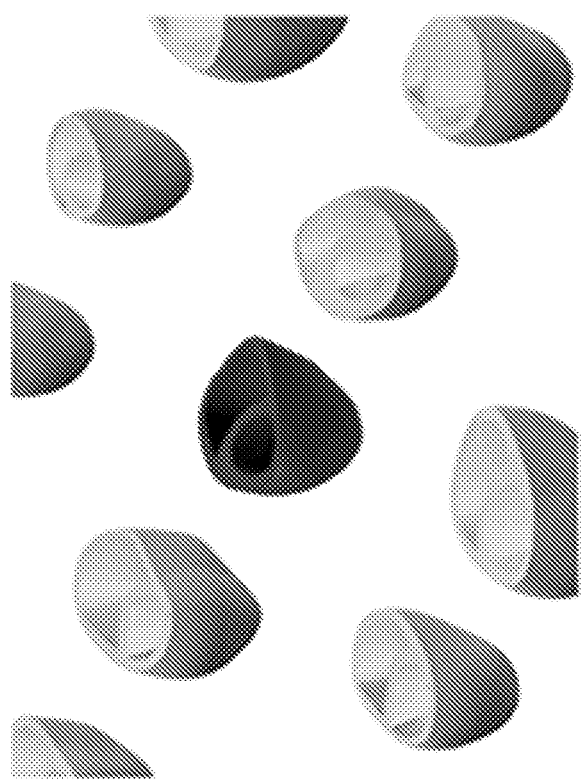
FIG. 3 depicts an example of a computational library of cardiac geometries which may be used to create simulation libraries of cardiac depolarization and repolarization. Within each geometry, various scar configurations, degrees of cardiac fibrosis and scar, conduction velocities, and other variables of cardiac arrhythmia simulation may be modified in accordance with some example embodiments.
Figure 4:
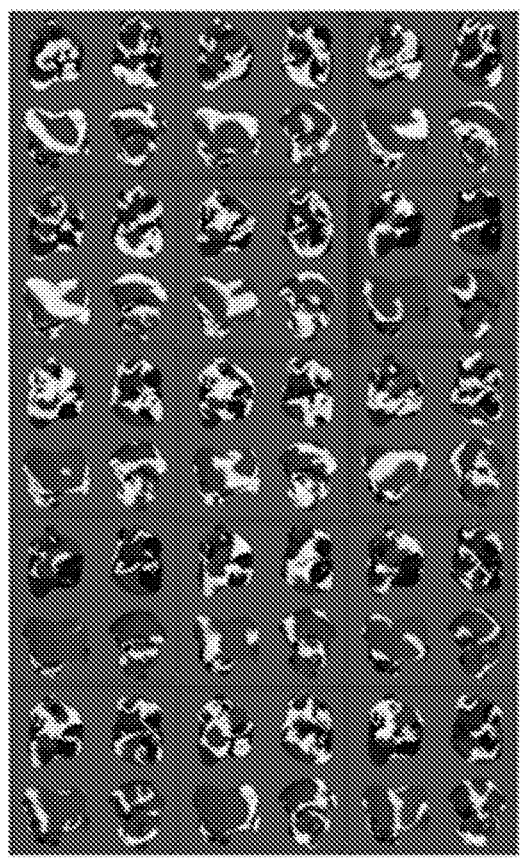
FIG. 4 depicts an example of a computational library of cardiac depolarization and repolarization simulations, in accordance with some example embodiments.

To further illustrate, FIG. 3 depicts an example of various cardiac geometries used to generate the computational library 125 with cardiac depolarization simulations (e.g., ventricular depolarization simulations) for a variety of scar configurations, conduction velocities, cardiac orientations, etc. FIG. 4 depicts another example of the computational library 125 with simulations of cardiac depolarization (e.g., leading wavefront of light areas) and repolarization (e.g., leading wavefront of dark areas).

Figure 13:
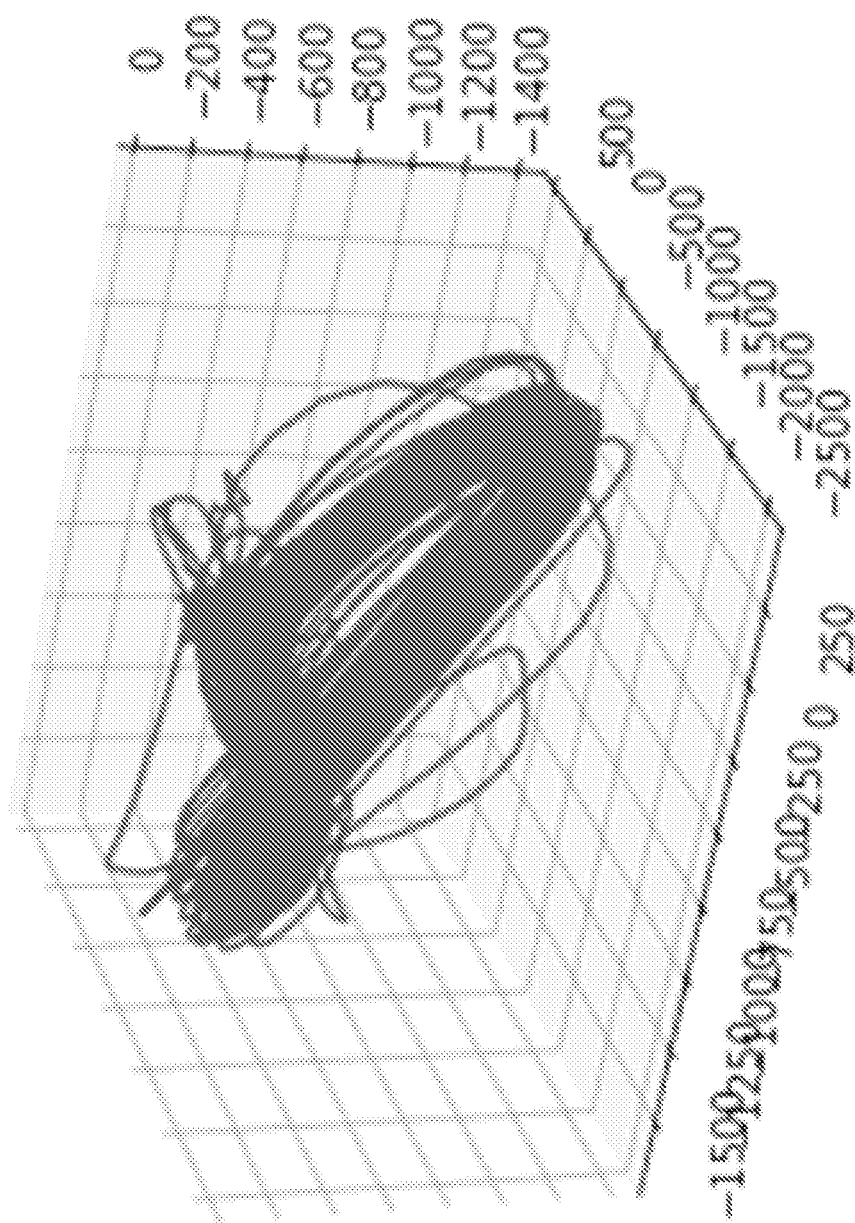
FIG. 13 depicts an example of a 3-dimensional plot of cardiac depolarization and cardiac repolarization, in accordance with some example embodiments.

In some example embodiments, the assessment engine 110 may identify, within the computational library 125, one or more simulations that correspond to the patient's electrical recordings. Examples of electrical recordings include an electrogram, body surface potential recordings (e.g., electrocardiographic imaging (ECGi)), a vectorgram, an electrocardiogram, an electroencephalogram, and a vectorcardiogram. FIG. 2(a) shows a 12-lead electrocardiogram (ECG) recording with optional supplemental electrogram recordings distributed around the torso, abdomen, neck, arms, and legs. The resulting electrograms are shown in FIG. 2(b). FIG. 13 depicts an example of a vectorcardiography (VCG) plot illustrating, as a continuous series of vectors, the magnitude and direction of the electrical forces generated by the patient's heart during depolarization and repolarization. The assessment engine 110 may identify, based at least on the patient's depolarization (e.g., the QRS complex observed in the patient's electrical recordings), one or more cardiac depolarization simulations (e.g., ventricular activation simulations) matching the patient's electrical recordings. Alternatively and/or additionally, the assessment engine 110 may identify, based at least on the patient's repolarization (e.g., the T wave observed in the patient's electrical recordings), one or more cardiac repolarization simulations (e.g., ventricular recovery simulations) matching the patient's electrical recordings. In some instances, the patient's electrical recordings may undergo one or more signal processing techniques before being compared to the simulations in the computational library. Examples of applicable signal processing techniques include recording, filtering, digitization, transformation, and spatial analysis.

Figure 11:
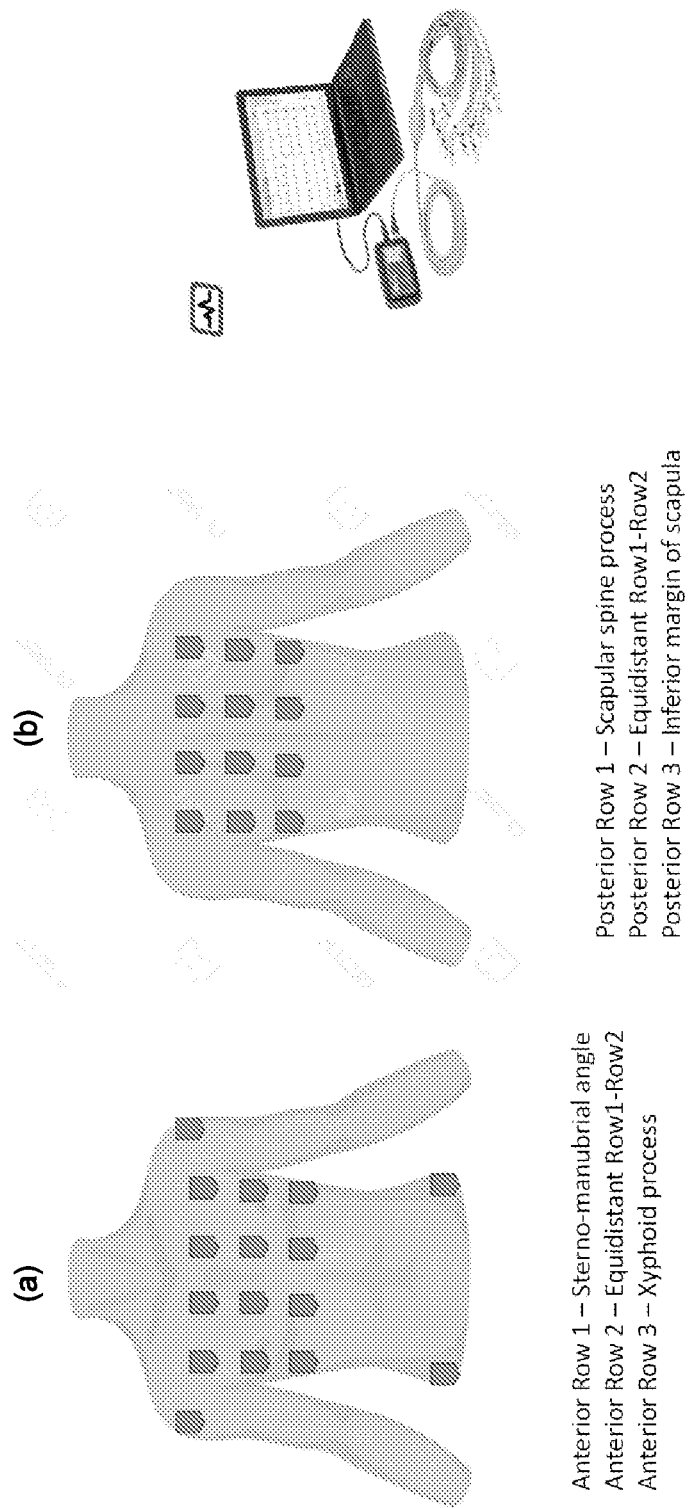
FIG. 11 depicts an example of an experimental setup for capturing the electrical recordings of a patient, in accordance with some example embodiments.

FIG. 11 depicts an example of a 30-lead electrocardiogram (ECG) setup for capturing the electrical recordings of a patient, in accordance with some example embodiments. As shown in FIG. 11, the 30-lead electrocardiogram (ECG) setup may include four portable harnesses with 24 unique precordial leads and 6 unique limb leads. Referring to FIG. 11(a), the 30-lead electrocardiogram (ECG) setup may include a first anterior row (of electrodes) positioned across the sterno-manubrial angle, a second anterior row positioned across the xyphoid process, and a third anterior row positioned equidistant between the first anterior row and the second anterior row. In addition, FIG. 11(b) shows that the 30-lead electrocardiogram (ECG) setup may include a first posterior row positioned across the scapular spine process, a second posterior row positioned across the inferior margin of scapula, and a third posterior row positioned equidistant between the first posterior row and the second posterior row.

Figure 12:
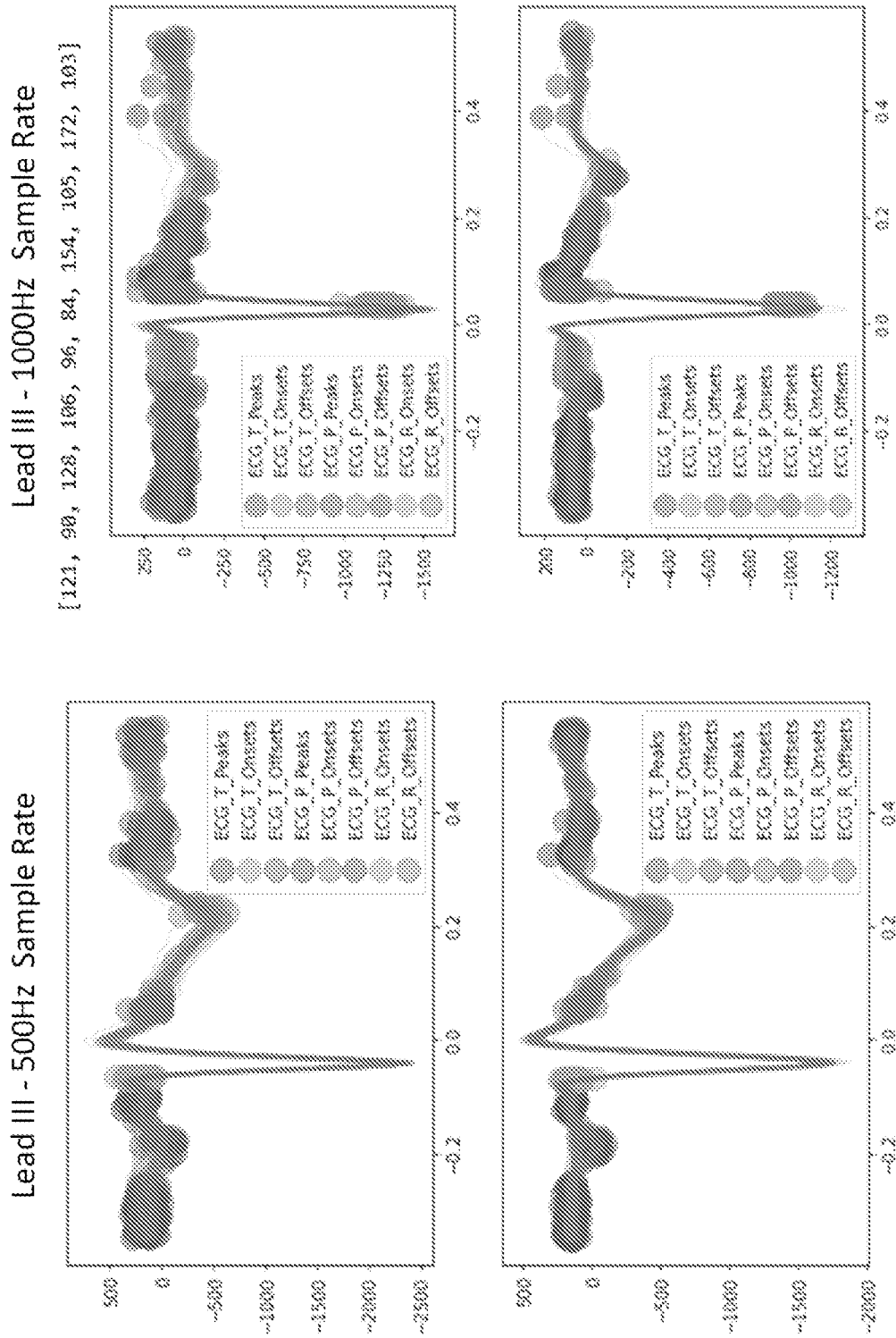
FIG. 12 depicts examples of data tracings, in accordance with some example embodiments.

FIG. 12 depicts examples of data tracings captured, for example, by the 30-lead electrocardiogram (ECG) setup shown in FIG. 11. For example, FIG. 12 shows data tracings for the same lead (e.g., Lead III) but at different sampling rates (e.g., 500 hertz and 1000 hertz). In some example embodiments, the assessment engine 110 may process data from each lead individually. In doing so, the assessment engine 110 may generate corresponding graphs and identify one or more peaks, peak onsets, and peak offsets present in the data. Moreover, the assessment engine 110 may extract one or more peak, peak onset, and/or peak offset points to determine measurements such as QT intervals, QT dispersion, and/or the like.

In some example embodiments, prior to matching the patient's electrocardiogram to one or more simulations in the computational library 125, the assessment engine 110 may first identify a subset of the simulations corresponding to the patient's anatomy such that the subsequent matching is performed within the subset of simulations instead of the entire computational library 125. For example, the assessment engine 110 may identify the subset of simulations corresponding to the patient's anatomy based on patient specific clinical data such as patient demographics and cardiac imaging. Examples of relevant imaging modalities include cardiac computed tomography cardiac magnetic resonance imaging (MRI), sestamibi imaging (nuclear scintigraphy), cardiac positron emission tomography and computed tomography scanning (cardiac PET/CT), 2-dimensional and 3-dimensional echocardiography, 3-dimensional electroanatomic mapping incorporating voltage mapping, electrogram mapping, activation mapping, entrainment mapping, isochronal late activation mapping, and impedance mapping.

Figure 5:
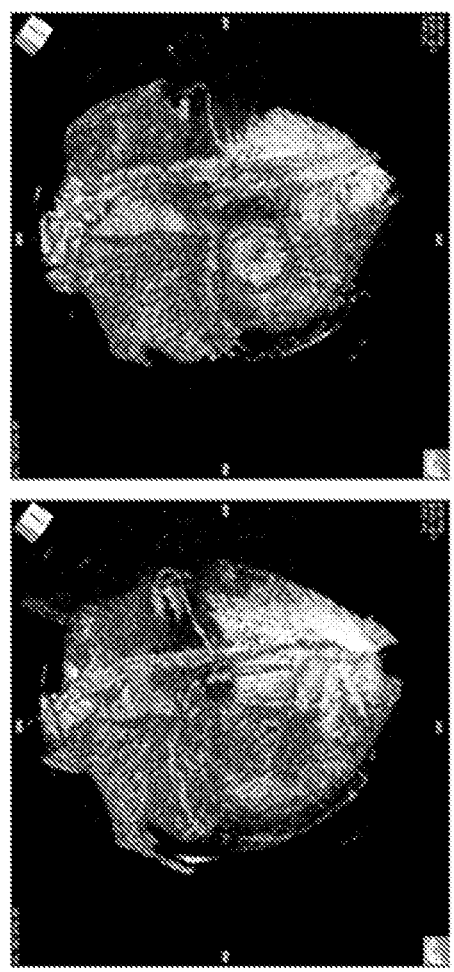
FIG. 5 depicts an example imaging modality for localization of scar tissue, borderzone tissue, normal tissue, chamber size, and myocardial contractility in accordance with some example embodiments.

Cardiac imaging data may be used to determine the locations of scar tissue, borderzone tissue, and normal tissue in the patient. For instance, FIG. 5 depicts a 3-dimensional volume rendering from 4-dimensional computed tomography (CT) with areas corresponding to borderzone tissue (e.g., between scar tissue and normal tissue) denoted by the dotted line. The area within the circle exhibits a relative lack of motion, which corresponds to dense scar tissue. Thus, in combination with patient demographics, the assessment engine 110 may use cardiac imaging data to eliminate simulations that are associated anatomies not sufficiently similar to the patient's anatomy and thus cannot be a match for the patient's electrical recordings. Doing so may increase the computational speed and efficiency of the subsequent matching to identify simulations that match the patient's electrical recordings.

In some instances where the patient's anatomy is not well represented in the computational library 125, the assessment engine 110 may generate a custom computational library for the patient that includes one or more patient specific cardiac repolarization simulations (e.g., ventricular activation simulations) and cardiac depolarization simulations (e.g., ventricular recovery simulations). For example, a custom computational library may be generated when the clinical data (e.g., demographics, cardiac imaging, and/or the like) associated with the simulations included in the computational library 125 are not sufficiently similar to the clinical data associated with the patient. As such, a custom computational library for the patient may be generated based on patient specific clinical data such as patient demographics and cardiac imaging.

In some example embodiments, a variety of technique may be applied in order to match one or more cardiac depolarization simulations (e.g., ventricular activation simulations) and cardiac repolarization simulations (e.g., ventricular recovery simulations) to the patient's electrical recordings. For example, the assessment engine 110 may apply one or more machine learning models trained to identify one or more cardiac depolarization simulations (e.g., ventricular activation simulations) and cardiac repolarization simulations (e.g., ventricular recovery simulations) matching the patient's electrical recordings. Examples of suitable machine learning models include a neural network, a regression model, an instance-based model, a regularization model, a decision tree, a random forest, a Bayesian model, a clustering model, an associative model, a dimensionality reduction model, an ensemble model, and/or the like.

In doing so, the assessment engine 110 may compare spatial data and/or temporal data. For instance, a 12-lead electrocardiogram (ECG) recording may include time series data in which the voltages measured by the electrodes are recorded at regular time intervals (e.g., every millisecond; 1000 Hz). To identify simulations matching the patient's 12-lead electrocardiogram (ECG) recording, the assessment engine 110 may apply a recurrent neural network (e.g., a long short term memory (LSTM) network and/or the like) capable of recognizing patterns present across two or more sequences of measurements. The recurrent neural network (RNN) may be trained, for example, to detect QRS complexes in one or more cardiac depolarization simulations (e.g., ventricular activation simulations) that match those present in the patient's 12-lead electrocardiogram (ECG) recording. Alternatively and/or additionally, the recurrent neural network may be trained to detect T waves in one or more cardiac repolarization simulations (e.g., ventricular recovery simulations) that match those present in the patient's 12-lead electrocardiogram (ECG) recording.

Upon identifying (or generating) the cardiac depolarization simulations (e.g., ventricular activation simulations) and cardiac repolarization simulations (e.g., ventricular recovery simulations) matching the patient's electrical recordings, the assessment engine 110 may apply the simulations to generate a 3-dimensional assessment for the patient. For example, the assessment engine 110 may determine, based at least on the cardiac depolarization simulations (e.g., ventricular activation simulations) and cardiac repolarization simulations (e.g., ventricular recovery simulations) matching the patient's electrical recordings, the magnitude and/or location(s) of the regions of increased spatial repolarization gradient, slow conduction, conduction block, or early activation. As shown in FIG. 14, the cardiac repolarization phase of a patient with ventricular arrhythmias may exhibit one or more abnormalities that are not present in the cardiac repolarization of a control patient. For instance, the presence of neighboring myocardium areas with above-threshold different rates of cardiac repolarization (e.g., a first area of long repolarization that is immediately adjacent to a second area of short repolarization) may be a potentially pro-arrhythmic condition. Sites of slow conduction are also known to perpetuate certain types of arrhythmias. And sites of early activation may be locations of pro-arrhythmic tissue. Accordingly, in some example embodiments, the assessment engine 110 may determine, based at least on the magnitude of the increased spatial repolarization gradient, an estimate of the patient's risk for cardiac arrhythmia (e.g., ventricular arrhythmia).

Figure 7:
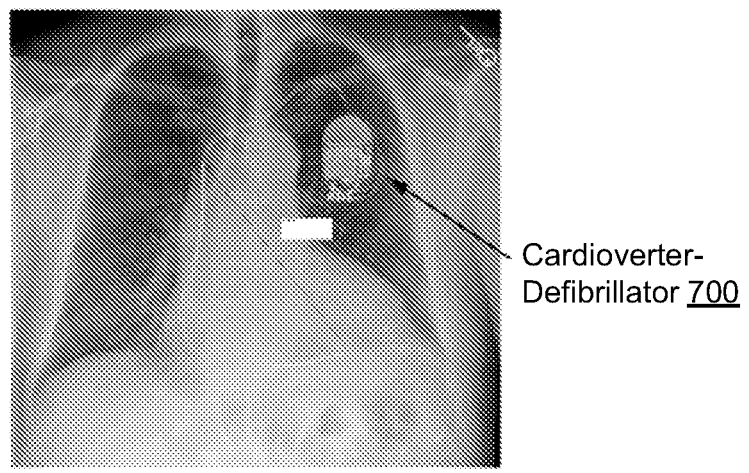
FIG. 7 depicts an example of a biventricular implantable cardioverter-defibrillator (ICD), in accordance with some example embodiments.
Figure 8:
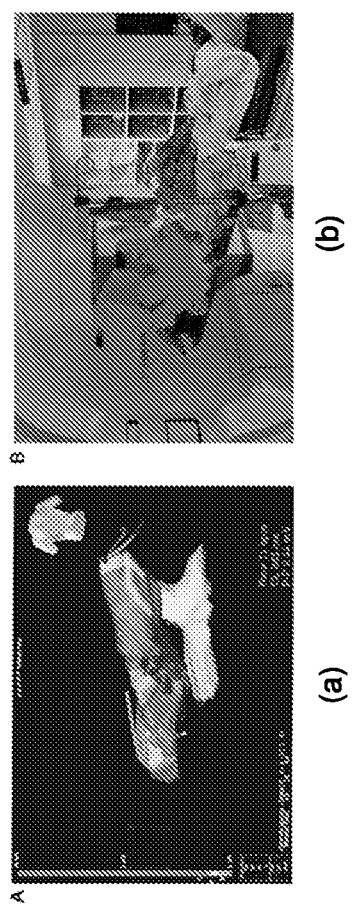
FIG. 8 depicts examples of targeted therapies for cardiac arrhythmia, in accordance with some example embodiments.

Furthermore, the assessment engine 110 may further determine, based at least on the magnitude and/or location(s) of the increased spatial repolarization gradient, a treatment plan for the patient. For example, the assessment engine 110 may determine, based at least on the magnitude of the increased spatial repolarization gradient, whether the patient may benefit from an implantable cardioverter-defibrillator or invasive electrophysiology study and ablation. FIG. 7 depicts a biventricular implantable cardioverter-defibrillator (ICD) 700 placed in a patient with cardiomyopathy and a left ventricular ejection fraction of less than 35%. Alternatively and/or additionally, the location(s) of increased spatial repolarization gradient, area of slow conduction, a protected conduction isthmus, or site of early activation may be used for determine a location for targeted therapies including, for example, radiofrequency catheter ablation, cryoablation, stereotactic ablative radiotherapy (SAbR) (or stereotactic body radiation therapy (SBRT)), and/or the like. FIG. 8(a) depicts an example of an electroanatomic map a ventricular tachycardia ablation with circular markers noting the ablation sites located at the mid-inferior left ventricle. FIG. 8(b) depicts a patient with refractory ventricular arrhythmias undergoing a stereotactic ablative radiotherapy (SAbR) procedure targeting sites at the anterior mitral annulus of the left ventricle.

Figure 6:
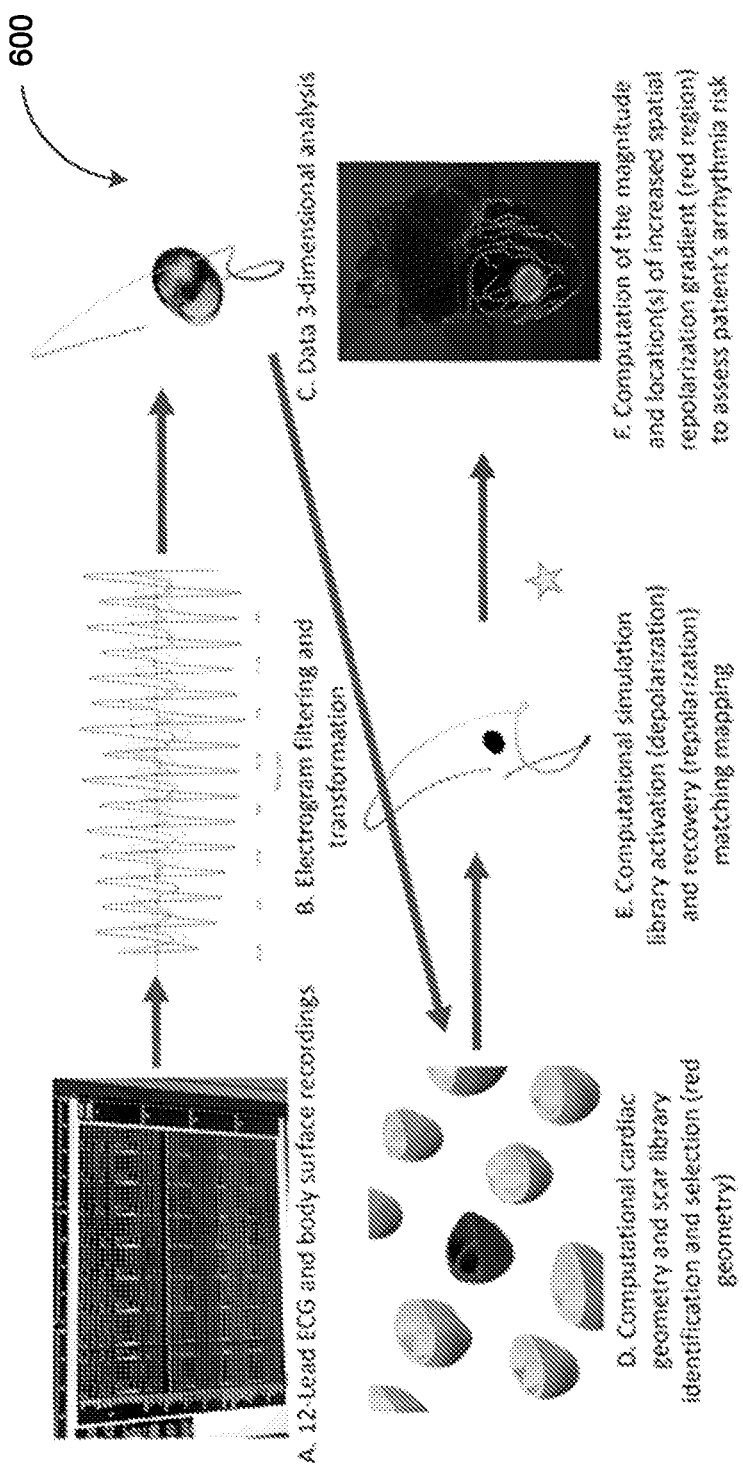
FIG. 6 depicts an example of a process for calculating the magnitude and location of regions of increased spatial repolarization gradient using non-invasive 12-lead electrocardiogram (ECG) data with or without body surface potential recordings, in accordance with some example embodiments.

FIG. 6 depicts an example of a process 600 for calculating the magnitude and location of regions of increased spatial repolarization gradient using non-invasive 12-lead electrocardiogram (ECG) data with or without body surface potential recordings, in accordance with some example embodiments. As shown in FIG. 6(A), a 12-lead electrocardiogram (ECG) recording may be performed for a patient with or without supplemental body surface potential recordings (e.g., around the torso, abdomen, neck, arms, and/or legs of the patient). At FIGS. 6(B) and 6(C), the resulting electrogram may be subjected to one or more signal processing techniques including, for example, recording, filtering, digitization, transformation, spatial analysis, and/or the like. At FIG. 6(D), a subset of the simulations from the computational library 125 that corresponds to the patient's anatomy may be identified such that the subsequent matching is performed within the subset of simulations instead of the entire computational library 125. At FIG. 6(E), cardiac depolarization simulations (e.g., ventricular activation simulations) and cardiac repolarization simulations (e.g., ventricular recovery simulations) matching the patient's 12-lead electrocardiogram (ECG) recording may be identified. At FIG. 6(F), the magnitude and/or location(s) of increased spatial repolarization gradient may be computed based on the cardiac depolarization simulations (e.g., ventricular activation simulations) and cardiac repolarization simulations (e.g., ventricular recovery simulations) matching the patient's 12-lead electrocardiogram (ECG) recording. As noted, the presence of neighboring myocardium areas with above-threshold different rates of cardiac repolarization (e.g., a first area of long repolarization that is immediately adjacent to a second area of short repolarization) may be a potentially pro-arrhythmic condition. Accordingly, the patient's risk for cardiac arrhythmia (e.g., ventricular arrhythmia) may be determined based at least on the magnitude of the increased spatial repolarization gradient. Moreover, one or more treatments suitable for the patient may be identified based at least on the magnitude and/or location(s) of the increased spatial repolarization gradient.

In some cases, the assessment engine 110 may further determine, based at least on the one or more cardiac depolarization simulations and cardiac repolarization simulations corresponding to the patient's electrical recordings, a presence and/or an absence of one or more regions of early activation, slow conduction, independent activation pathways, late activation, protected isthmuses of conduction, and/or conduction block. The treatment plan for the patient may further take into account these regions of early activation, slow conduction, independent activation pathways, late activation, and/or conduction block. For example, the assessment engine 110 may generate a treatment plan targeting, individually or in groups, the one or more regions of early activation, slow conduction, independent activation pathways, late activation, and/or conduction block. Alternatively and/or additionally, the assessment engine 110 may determine whether the patient is a candidate for one or more drug therapies based at least on the presence and/or absence of the one or more regions of early activation, slow conduction, independent activation pathways, late activation, and/or conduction block.

Figure 9:
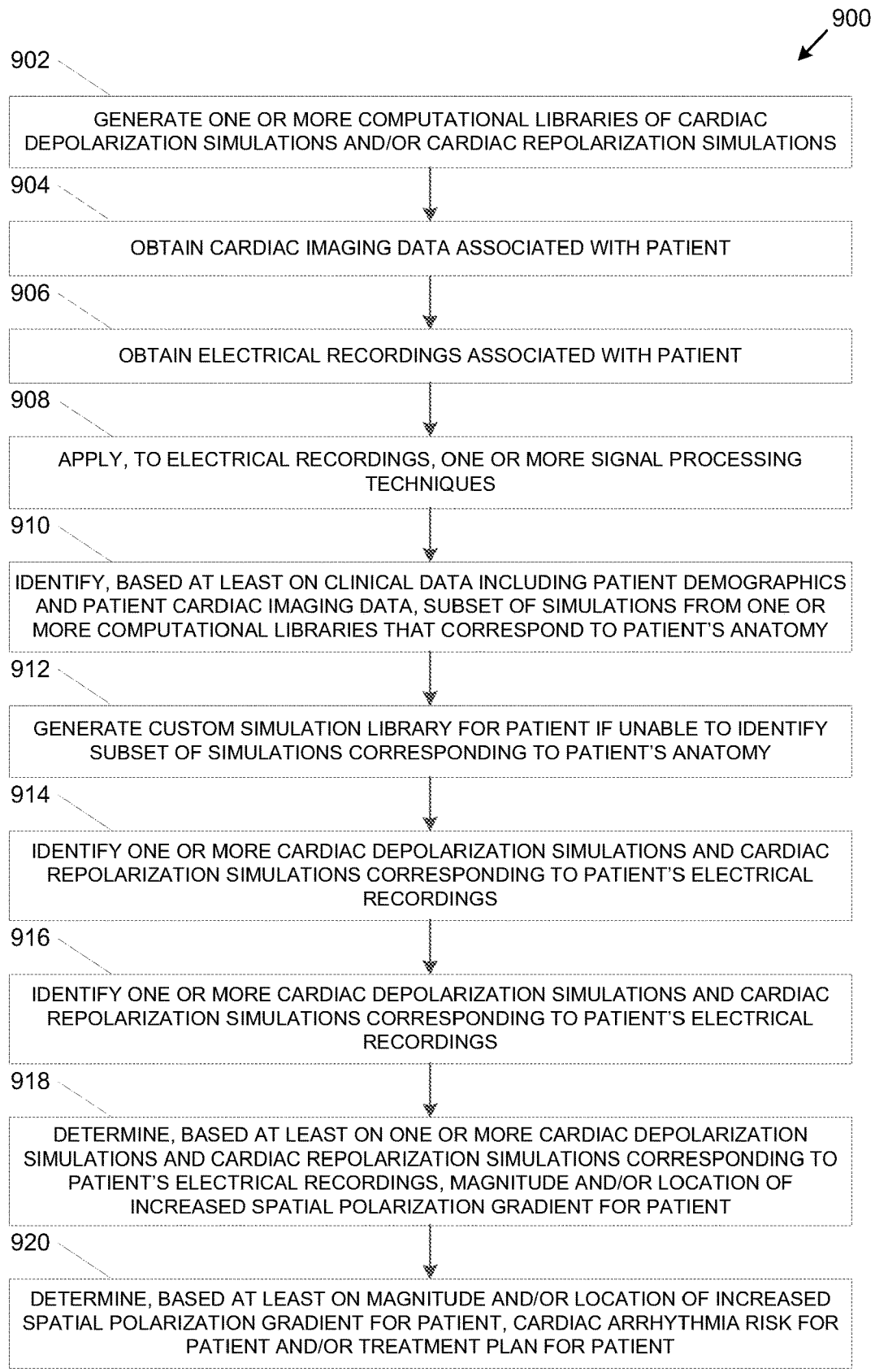
FIG. 9 depicts a flowchart illustrating an example of a process for non-invasive arrhythmia risk stratification, in accordance with some example embodiments.
Figure 10:
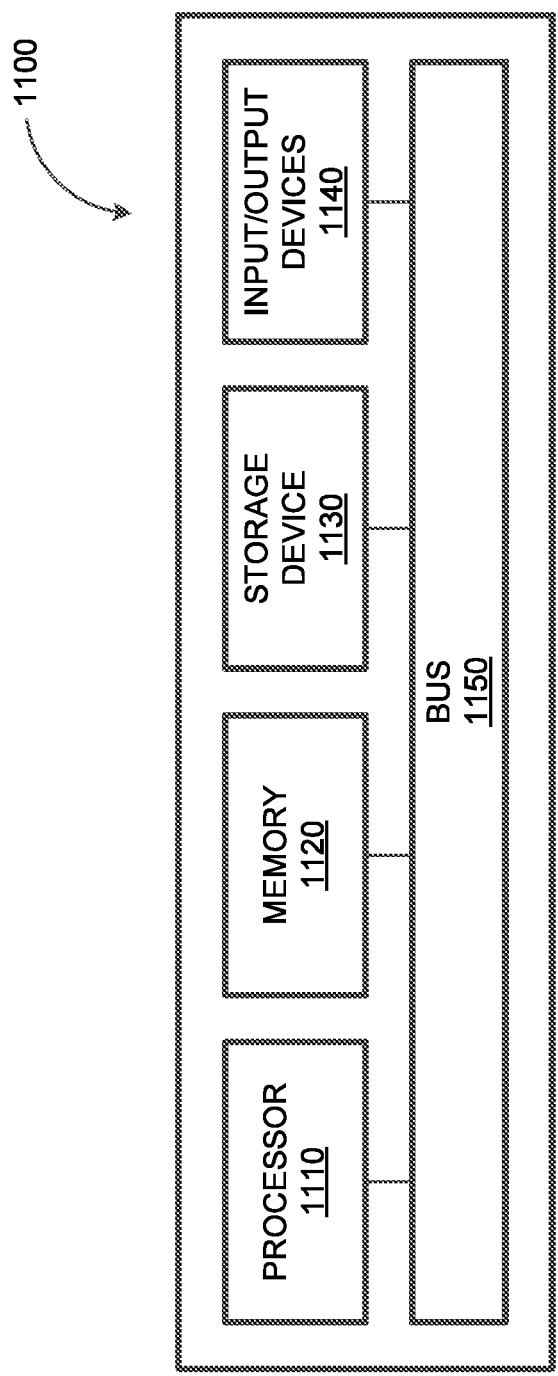
FIG. 10 depicts a block diagram illustrating a computing system, in accordance with some example embodiments.

FIG. 9 depicts a flowchart illustrating an example of a process 900 for non-invasive cardiac arrhythmia risk stratification, in accordance with some example embodiments. Referring to FIGS. 1 and 9, the process 900 may be performed by the assessment engine 110 in order to determine a patient's risk for cardiac arrhythmia.

At 902, the assessment engine 110 may generate one or more computational libraries of cardiac depolarization simulations and/or cardiac repolarization simulations. For example, in some example embodiments, the assessment engine 110 may generate the computational library 125 to include cardiac depolarization simulations (e.g., ventricular activation simulations) for various cardiac geometries, cardiac orientations, scar configurations, degrees of cardiac fibrosis and scar, depolarization patterns, activation types (e.g. left bundle branch block, right bundle branch block, left anterior fascicular block, left posterior fascicular block, premature ventricular complexes, ventricular tachycardia, and ventricular fibrillation), and combinations thereof. Alternatively and/or additionally, the assessment engine 110 may generate the computational library 125 to include cardiac repolarization simulations (e.g., ventricular recovery simulations) for various cardiac geometries, cardiac orientations, scar configurations, degrees of cardiac fibrosis and scar, depolarization patterns, activation types (e.g. left bundle branch block, right bundle branch block, left anterior fascicular block, left posterior fascicular block, premature ventricular complexes, ventricular tachycardia, and ventricular fibrillation), and combinations thereof. In some instances, the computational library 125 may include a first computational library of cardiac depolarization simulations (e.g., ventricular activation simulations) and a second computational library of cardiac repolarization simulations (e.g., ventricular recovery simulations).

At 904, the assessment engine 110 may obtain cardiac imaging data associated with a patient. For example, the assessment engine 110 may obtain cardiac imaging data in a variety of imaging modalities including, for example, cardiac computed tomography (e.g., 3-dimensional volume rendering from 4-dimensional computed tomography shown in FIG. 5), cardiac magnetic resonance imaging (MRI), sestamibi imaging (nuclear scintigraphy), cardiac positron emission tomography and computed tomography scanning (cardiac PET/CT), 2-dimensional and 3-dimensional echocardiography, 3-dimensional electroanatomic mapping incorporating voltage mapping, electrogram mapping, activation mapping, entrainment mapping, isochronal late activation mapping, and impedance mapping. In some example embodiments, the cardiac imaging data associated with the patient may enable the assessment engine 110 to determine the locations of scar tissue, borderzone tissue, and normal tissue in the patient.

Figure 2:
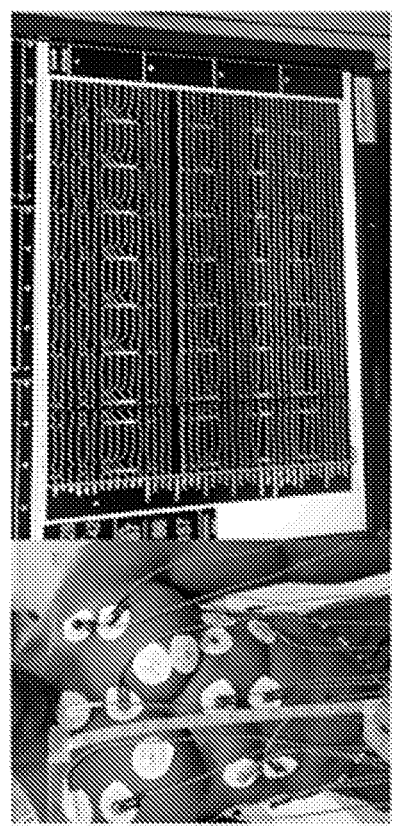
FIG. 2 depicts an example of a non-invasive 12-lead electrocardiogram (ECG) and supplemental body-surface electrograms for computing the spatial repolarization gradient and risk of cardiac arrhythmias, in accordance with some example embodiments.

At 906, the assessment engine 110 may obtain electrical recordings associated with the patient. In some example embodiments, the assessment engine 110 may obtain a variety of electrical recordings for the patient including, for example, electrograms, vectorgrams, electrocardiograms, electroencephalograms, vectorcardiogram, and/or the like. FIG. 2 depicts a 12-lead electrocardiogram (ECG) recording, which is one example of electrical recordings that may be obtained by the assessment engine 110. As shown in FIG. 2, the 12-lead electrocardiogram (ECG) recording may be performed with (or without) supplemental body surface potential recordings distributed, for example, around the patient's torso, abdomen, neck, arms, and/or legs.

At 908, the assessment engine 110 may apply, to the electrical recordings, one or more signal processing techniques. In some example embodiments, the assessment engine 110 may apply, to the patient's electrical recordings (e.g., 12-lead electrocardiogram (ECG) recording) a variety of signal processing techniques include, for example, recording, filtering, digitization, transformation, spatial analysis, and/or the like. The processing of the electrical recordings may be optional and the matching of the electrical recordings may be performed without any signal processing.

At 910, the assessment engine 110 may identify, based at least on clinical data including patient demographics and patient cardiac imaging data, a subset of simulations from the one or more computational libraries that correspond to the patient's anatomy. In some example embodiments, prior to matching the patient's electrocardiogram to one or more simulations in the computational library 125, the assessment engine 110 may first identify a subset of the simulations corresponding to the patient's anatomy. As such, subsequent matching to identify matching simulations may be performed within the subset of simulations instead of the entire computational library 125. The assessment engine 110 may identify the subset of simulations corresponding to the patient's anatomy based on patient specific clinical data such as patient demographics and cardiac imaging. For example, the assessment engine 110 may eliminate, based at least on the patient's demographics and cardiac imaging data, simulations that are associated anatomies not sufficiently similar to the patient's anatomy and thus cannot be a match for the patient's electrical recordings. As noted, the assessment engine 110 may first identify a subset of simulations in order to increase the computational speed and efficiency of the subsequent matching to identify simulations that match the patient's electrical recordings. However, it should be appreciated that selecting a subset of simulations that correspond to the patient's anatomy is optional optimization and the subsequent matching may instead be performed on the entire computational library 125 without first identifying the subset of simulations that correspond to the patient's anatomy.

At 912, the assessment engine 110 may generate a custom simulation library for the patient if the assessment engine 110 fails to identify the subset of simulations corresponding to the patient's anatomy. In some instances, it may be possible that the patient's anatomy is not well represented in the computational library 125. In those scenarios, the assessment engine 110 may generate a custom computational library for the patient that includes one or more patient specific cardiac repolarization simulations (e.g., ventricular activation simulations) and cardiac depolarization simulations (e.g., ventricular recovery simulations). For example, a custom computational library may be generated when the clinical data (e.g., demographics, cardiac imaging, and/or the like) associated with the simulations included in the computational library 125 are not sufficiently similar to the clinical data associated with the patient. As such, the assessment engine 110 may generate, based on patient specific clinical data such as patient demographics and cardiac imaging, a custom computational library for the patient.

At 914, the assessment engine 110 may identify one or more cardiac depolarization simulations and cardiac repolarization simulations corresponding to the patient's electrical recordings. For example, the assessment engine 110 may identify, based at least on the patient's depolarization (e.g., the QRS complex observed in the patient's electrical recordings), one or more cardiac depolarization simulations (e.g., ventricular activation simulations) matching the patient's electrical recordings. Alternatively and/or additionally, the assessment engine 110 may identify, based at least on the patient's repolarization (e.g., the T wave observed in the patient's electrical recordings), one or more cardiac repolarization simulations (e.g., ventricular recovery simulations) matching the patient's electrical recordings. This matching be performed by comparing the patient's electrical recordings to at least a portion of the simulations included in the computational library 125 or, optionally, to a subset of simulations determined to correspond to the patient's anatomy. The assessment engine 110 may apply a variety of technique identify one or more cardiac depolarization simulations (e.g., ventricular activation simulations) and cardiac repolarization simulations (e.g., ventricular recovery simulations) matching the patient's electrical recordings. For instance, the assessment engine 110 may apply one or more machine learning models trained to identify one or more cardiac depolarization simulations (e.g., ventricular activation simulations) and cardiac repolarization simulations (e.g., ventricular recovery simulations) matching the patient's electrical recordings.

At 918, the assessment engine 110 may determine, based at least on the one or more cardiac depolarization simulations and cardiac repolarization simulations corresponding to the patient's electrical recordings, a magnitude and/or a location of increased spatial repolarization gradient for the patient. A spatial repolarization gradient may be present when neighboring myocardium areas exhibit an above-threshold difference in rate of cardiac repolarization. Accordingly, the assessment engine 110 may identify, based at least on the one or more cardiac depolarization simulations and cardiac repolarization simulations corresponding to the patient's electrical recordings, a first myocardium area of long repolarization that is immediately adjacent to a second myocardium area of short repolarization. Moreover, the assessment engine 110 may determine, based at least on the one or more cardiac depolarization simulations and cardiac repolarization simulations corresponding to the patient's electrical recordings, a difference between a first repolarization rate of the first area and a second repolarization rate of the second area.

At 920, the assessment engine 110 may determine, based at least on the magnitude and/or the location of increased spatial repolarization gradient, a cardiac arrhythmia risk for the patient and/or a treatment plan for the patient. For example, the assessment engine 110 may identify, based at least on neighboring myocardium areas with above-threshold different rates of cardiac repolarization (e.g., a first area of long repolarization that is immediately adjacent to a second area of short repolarization), a potentially pro-arrhythmic condition that is likely to result in an electrical wavebreak, reentry, and life-threatening arrhythmia. Accordingly, the assessment engine 110 may identify, based at least on the magnitude of the increased spatial repolarization gradient, the patient's risk for cardiac arrhythmia (e.g., ventricular arrhythmia). In some instances, the assessment engine 110 may further identify, based on the magnitude and/or location(s) of the increased spatial repolarization gradient one or more treatments suitable for the patient. For instance, the magnitude of the increased spatial repolarization gradient, extent of slow conduction, or early activation may enable the assessment engine 110 to determine whether the patient will benefit from a cardioverter-defibrillator implantation or an invasive electrophysiology study and ablation. Alternatively and/or additionally, the location(s) of increased spatial repolarization gradient may be used for determining the location of targeted therapies including, for example, catheter ablation, stereotactic ablative radio-therapy (SAbR) (or stereotactic body radiation therapy (SBRT)), and/or the like.

FIG. 11 depicts a block diagram illustrating a computing system 1100, in accordance with some example embodiments. Referring to FIGS. 1 and 11, the computing system 1100 can be used to implement the assessment engine 110 and/or any components therein.

As shown in FIG. 11, the computing system 1100 can include a processor 1110, a memory 1120, a storage device 1130, and input/output device 1140. The processor 1110, the memory 1120, the storage device 1130, and the input/output device 1140 can be interconnected via a system bus 1150. The processor 1110 is capable of processing instructions for execution within the computing system 1100. Such executed instructions can implement one or more components of, for example, the assessment engine 110. In some implementations of the current subject matter, the processor 1110 can be a single-threaded processor. Alternately, the processor 1110 can be a multi-threaded processor. The processor 1110 is capable of processing instructions stored in the memory 1120 and/or on the storage device 1130 to display graphical information for a user interface provided via the input/output device 1140.

The memory 1120 is a computer readable medium such as volatile or non-volatile that stores information within the computing system 1100. The memory 1120 can store data structures representing configuration object databases, for example. The storage device 1130 is capable of providing persistent storage for the computing system 1100. The storage device 1130 can be a floppy disk device, a hard disk device, an optical disk device, or a tape device, or other suitable persistent storage means. The input/output device 1140 provides input/output operations for the computing system 1100. In some implementations of the current subject matter, the input/output device 1140 includes a keyboard and/or pointing device. In various implementations, the input/output device 1140 includes a display unit for displaying graphical user interfaces.

According to some implementations of the current subject matter, the input/output device 1140 can provide input/output operations for a network device. For example, the input/output device 1140 can include Ethernet ports or other networking ports to communicate with one or more wired and/or wireless networks (e.g., a local area network (LAN), a wide area network (WAN), the Internet).

In some implementations of the current subject matter, the computing system 1100 can be used to execute various interactive computer software applications that can be used for organization, analysis and/or storage of data in various (e.g., tabular) format. Alternatively, the computing system 1100 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, and/or the like. The applications can include various add-in functionalities or can be standalone computing products and/or functionalities. Upon activation within the applications, the functionalities can be used to generate the user interface provided via the input/output device 1140. The user interface can be generated and presented to a user by the computing system 1100 (e.g., on a computer screen monitor, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random-access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
at least one processor; and
at least one memory including program code which when executed by the at least one processor provides operations comprising:
generating a computational library that includes, for each of a plurality of cardiac geometries, a cardiac repolarization simulation;
accessing an electrical recording of a patient;
identifying, within the computational library, a cardiac repolarization simulation corresponding to the electrical recording of the patient;
determining, based at least on the cardiac repolarization simulation, one or more regions exhibiting an increased spatial repolarization gradient in which a ratio of a difference between a first repolarization rate of a first area of a myocardium of the patient a second repolarization rate of a second region of the myocardium, and a spatial distance between the first region and the second region exceeds a threshold value;
determining, based at least on a magnitude of the increased spatial repolarization gradient, a risk of cardiac arrhythmia for the patient; and
determining, based at least on the magnitude of the increased spatial repolarization gradient, a treatment plan for the patient.

2. The system of claim 1, wherein the treatment plan is determined to include, based at least the magnitude of the increased spatial repolarization gradient, a cardioverter-defibrillator implantation or an invasive electrophysiology study and ablation.

3. The system of claim 1, wherein the treatment plan includes determining, based at least on a location of the one or more regions of increased spatial repolarization gradient, a location for a targeted therapy.

4. The system of claim 3, wherein the targeted therapy includes catheter ablation and/or stereotactic ablative radiotherapy (SAbR).

5. The system of claim 1, wherein the operations further comprise:
identifying, based at least on clinical data associated with the patient, a subset of simulations from the computational library that correspond to an anatomy of the patient wherein the identifying of the cardiac repolarization simulation is based on the subset of simulations.

6. The system of claim 5, wherein the clinical data includes cardiac imaging data indicating one or more locations of scar tissue, borderzone tissue, and normal tissue, cardiac chamber size, the presence of hypertrophy or dilation, locations of fibrosis, regions of normal and abnormal contractility, or regions of wall thinning.

7. The system of claim 5, wherein the operations further comprise: in response to failing to identify the subset of simulations corresponding to the anatomy of the patient, generating, based at least on the clinical data of the patient, a custom computational library that includes one or more cardiac repolarization simulations specific to the anatomy of the patient.

8. The system of claim 1, wherein the operations further comprise applying a machine learning model trained to determine that the cardiac repolarization simulation matches the electrical recording of the patient.

9. The system of claim 8, wherein the machine learning model comprises a neural network, a regression model, an instance-based model, a regularization model, a decision tree, a random forest, a Bayesian model, a clustering model, an associative model, a dimensionality reduction model, and/or an ensemble model.

10. The system of claim 1, wherein the electrical recording comprises one or more of an electrogram, a vectorcardiogram, an electrocardiogram, an electroencephalogram, or a vectorcardiogram.

11. The system of claim 10, wherein the electrical recording further includes one or more body surface potential recordings.

12. The system of claim 1, wherein the electrical recording comprises an electrocardiographic imaging (ECGi) recording system including one or more body surface potential recordings.

13. The system of claim 1, wherein the operations further comprise:
determining, based at least on the cardiac repolarization simulation, one or more regions of early activation, slow conduction, independent activation pathways, late activation, protected conduction isthmuses, and/or conduction block; and
determining, based at least on a presence and/or an absence of the one or more regions of early activation, slow conduction, independent activation pathways, late activation, protected conduction isthmuses, and/or conduction block, the risk of cardiac arrhythmia for the patient.

14. The system of claim 13, wherein the operations further comprise:
determining, based at least on the one or more regions of early activation, slow conduction, independent activation pathways, late activation, protected conduction isthmuses, and/or conduction block, the treatment plan for the patient.

15. The system of claim 14, wherein the treatment plan targets, individually or in groups, the one or more regions of early activation, slow conduction, independent activation pathways, late activation, protected conduction isthmuses, and/or conduction block.

16. The system of claim 14, wherein the treatment plan is determined to include one or more drug therapies based at least on the presence and/or the absence of the one or more regions of early activation, slow conduction, independent activation pathways, late activation, protected conduction isthmuses, and/or conduction block.

17. A computer-implemented method, comprising:
generating a computational library that includes, for each of a plurality of cardiac geometries, a cardiac depolarization simulation and repolarization simulation;
accessing an electrical recording of a patient;
identifying, within a computational library, a cardiac depolarization simulation and a cardiac repolarization simulation corresponding to the electrical recording of the patient;
determining, based at least on the cardiac depolarization simulation and the cardiac repolarization simulation, one or more regions exhibiting an increased spatial repolarization gradient in which a ratio of a difference between a first repolarization rate of a first area of a myocardium of the patient a second repolarization rate of a second area of the myocardium, and a spatial distance between the first region and the second region exceeds a threshold value; and
determining, based at least on a magnitude of the increased spatial repolarization gradient, a risk of cardiac arrhythmia for the patient.

18. The method of claim 17, further comprising determining, based at least on the magnitude of the increased spatial repolarization gradient, a treatment plan for the patient.

19. The method of claim 18, wherein the treatment plan is determined to include, based at least the magnitude of the increased spatial repolarization gradient, a cardioverter-defibrillator implantation or an invasive electrophysiology study and ablation.

20. The method of claim 18, wherein the treatment plan includes determining, based at least on a location of the one or more regions of increased spatial repolarization gradient, a location for a targeted therapy.

21. The method of claim 20, wherein the targeted therapy includes catheter ablation and/or stereotactic ablative radiotherapy (SAbR).

22. The method of claim 17, wherein the cardiac depolarization simulation comprises a ventricular activation simulation, and wherein the cardiac repolarization simulation comprises a ventricular recovery simulation.

23. The method of claim 17, further comprising:
identifying, based at least on clinical data associated with the patient, a subset of simulations from the computational library that correspond to an anatomy of the patient; and
identifying, within the subset of simulations corresponding to the anatomy of the patient, the cardiac depolarization simulation and the cardiac repolarization simulation corresponding to the electrical recording of the patient.

24. The method of claim 23, wherein the clinical data includes patient demographics.

25. The method of claim 23, wherein the clinical data includes cardiac imaging data indicating one or more locations of scar tissue, borderzone tissue, and normal tissue, cardiac chamber size, the presence of hypertrophy or dilation, locations of fibrosis, regions of normal and abnormal contractility, and/or regions of wall thinning.

26. The method of claim 23, further comprising:
in response to failing to identify the subset of simulations corresponding to the anatomy of the patient, generating, based at least on the clinical data of the patient, a custom computational library that includes one or more cardiac depolarization simulations and/or cardiac repolarization simulations specific to the anatomy of the patient.

27. The method of claim 17, further comprising applying a machine learning model trained to determine that the cardiac repolarization simulation and the cardiac depolarization simulation match the electrical recording of the patient.

28. The method of claim 27, wherein the machine learning model comprises a neural network, a regression model, an instance-based model, a regularization model, a decision tree, a random forest, a Bayesian model, a clustering model, an associative model, a dimensionality reduction model, and/or an ensemble model.

29. The method of claim 17, further comprising:
determining, based at least on the cardiac depolarization simulation and the cardiac repolarization simulation, one or more regions of early activation, slow conduction, independent activation pathways, late activation, protected conduction isthmuses, and/or conduction block; and
determining, based at least on a presence and/or an absence of the one or more regions of early activation, slow conduction, independent activation pathways, late activation, protected conduction isthmuses, and/or conduction block, the risk of cardiac arrhythmia for the patient.

30. The method of claim 29, further comprising:
determining, based at least on the one or more regions of early activation, slow conduction, independent activation pathways, late activation, protected conduction isthmuses, and/or conduction block, a treatment plan for the patient.

31. The method of claim 30, wherein the treatment plan targets, individually or in groups, the one or more regions of early activation, slow conduction, independent activation pathways, late activation, protected conduction isthmuses, and/or conduction block.

32. The method of claim 30, wherein the treatment plan is determined to include one or more drug therapies based at least on the presence and/or the absence of the one or more regions of early activation, slow conduction, independent activation pathways, late activation, protected conduction isthmuses, and/or conduction block.

33. An apparatus, comprising:
means for generating a computational library that includes, for each of a plurality of cardiac geometries, a cardiac depolarization simulation and repolarization simulation;
means for accessing an electrical recording of a patient;
means for identifying, within a computational library, a cardiac depolarization simulation and a cardiac repolarization simulation corresponding to an electrical recording of a patient;
means for determining, based at least on the cardiac depolarization simulation and the cardiac repolarization simulation, one or more regions of increased spatial repolarization gradient in which a first area of a myocardium of the patient exhibits a first repolarization rate that differs from a second repolarization rate of a second area of the myocardium by an amount then divided by the spatial distance between the two regions, by a threshold value; and
means for determining, based at least on a magnitude of the increased spatial repolarization gradient, a risk of cardiac arrhythmia for the patient.

34. A method, comprising:
performing by a system that includes at least one processor and a memory including program code which when executed by the at least one processor provides operations comprising:
identifying, within a computational library, a cardiac repolarization simulation corresponding to an electrical recording of a patient;
determining, based at least on the cardiac repolarization simulation, one or more regions exhibiting an increased spatial repolarization gradient in which a ratio of a difference between a first repolarization rate of a first region of a myocardium of the patient a second repolarization rate of a second region of the myocardium, and a spatial distance between the first region and the second region exceeds a threshold value;
determining, based at least one a magnitude of the increased spatial repolarization gradient, a risk of cardiac arrhythmia for the patient; and
determining, based at least on the magnitude of the increased spatial repolarization gradient, a treatment plan for the patient that includes performing an ablation to treat a source of a cardiac arrhythmia; and performing the ablation on the patient in accordance with the treatment plan.

35. The method of claim 34 wherein the identifying includes applying a neural network that is trained to identify the cardiac repolarization simulation that match electrical recording of the patient.

36. The method of claim 35 wherein the electrical recording is an electrocardiogram that includes a voltage recorded at every millisecond.

37. The method of claim 35 wherein the electrical recording is an electrocardiogram that includes 500 voltages per second.

38. The system of claim 1 wherein the system further includes an ablation device and the operations comprise identifying a source of a cardiac arrhythmia and controlling the performing of an ablation targeting the source of the cardiac arrhythmia.

39. The system of claim 38 wherein the ablation is performed using stereotactic ablative radiotherapy.

40. The system of claim 38 wherein the ablation is performed using an ablation catheter.

41. The method of claim 34 wherein the ablation is a pulsed field ablation.

42. The method of claim 34 wherein the ablation is performed using stereotactic ablative radiotherapy.

43. The method of claim 34 wherein the ablation is performed using a catheter.

44. The method of claim 34 wherein the program code when executed by the at least one processor further provides operations comprising:
   determining, based at least on the cardiac repolarization simulation, one or more regions of early activation, slow conduction, independent activation pathways, late activation, protected conduction isthmuses, and/or conduction block and
   determining, based at least on a presence and/or an absence of the one or more regions of early activation, slow conduction, independent activation pathways, late activation, protected conduction isthmuses, and/or conduction block, the risk of cardiac arrhythmia for the patient.

45. The method of claim 34 wherein the program code when executed by the at least one processor provides operations further comprising generating a computational library that includes, for each of a plurality of cardiac geometries, a cardiac depolarization simulation.

46. A method, comprising:
   performing by a system that includes at least one processor and a memory including program code which when executed by the at least one processor provides operations comprising:
      identifying, within a computational library, a cardiac repolarization simulation corresponding to an electrical recording of a patient;
      determining, based at least one the cardiac repolarization simulation, one or more regions exhibiting an increased spatial repolarization gradient in which a ratio of a difference between a first repolarization rate of a first region of a myocardium of the patient a second repolarization rate of a second region of the myocardium, and a spatial distance between the first region and the second region exceeds a threshold value;
      determining, based at least on a magnitude of the increased spatial repolarization gradient, a risk of cardiac arrhythmia for the patient; and
      determining, based at least on the magnitude of the increased spatial repolarization gradient, a treatment plan for the patient that includes a cardioverter-defibrillator implantation to treat a cardiac arrhythmia; and
   implanting a cardioverter defibrillator in the patient in accordance with the treatment plan.

47. The method of claim 46 wherein the program code when executed by the at least one processor provides operations further comprising generating a computational library that includes, for each of a plurality of cardiac geometries, a cardiac depolarization simulation and repolarization simulation.

48. A method, comprising:
   performing by a system that includes at least one processor and a memory including program code which when executed by the at least one processor provides operations comprising:
      identifying, within a computational library, a cardiac repolarization simulation corresponding to an electrical recording of a patient;
      determining, based at least one the cardiac repolarization simulation, one or more regions exhibiting an increased spatial repolarization gradient in which a ratio of a difference between a first repolarization rate of a first region of a myocardium of the patient a second repolarization rate of a second region of the myocardium, and a spatial distance between the first region and the second region exceeds a threshold value;
      determining, based at least on a magnitude of the increased spatial repolarization gradient, a risk of cardiac arrhythmia for the patient; and
      determining, based at least on the magnitude of the increased spatial repolarization gradient, a treatment plan for the patient that includes one or more of a cardiac ablation, a cardioverter-defibrillator implantation, a drug therapy, or an invasive electrophysiology study to treat a cardiac arrhythmia; and
   treating the patient in accordance with the treatment plan, the treating including one or more of performing a cardiac ablation, implanting a cardioverter defibrillator, administering the drug therapy, and performing the invasive electrophysiology study.

49. The method of claim 48 wherein the program code when executed by the at least one processor provides operations further comprising generating a computational library that includes, for each of a plurality of cardiac geometries, a repolarization simulation.

* * * * *